United States Patent [19]

Lundblom

[11] Patent Number: 4,672,039
[45] Date of Patent: Jun. 9, 1987

[54] APPARATUS FOR REGISTERING THE PRESENCE OF BACTERIA, PARTICULARLY IN FIELD CONDITIONS

[75] Inventor: Einar Lundblom, Rockneby, Sweden

[73] Assignee: AB Sangtec Medical, Sweden

[21] Appl. No.: 787,791

[22] PCT Filed: Feb. 11, 1985

[86] PCT No.: PCT/SE85/00067
§ 371 Date: Oct. 4, 1985
§ 102(e) Date: Oct. 4, 1985

[87] PCT Pub. No.: WO85/03518
PCT Pub. Date: Aug. 15, 1985

[30] Foreign Application Priority Data
Feb. 10, 1984 [SE] Sweden ............... 8400696

[51] Int. Cl.⁴ .................................. C12M 1/34
[52] U.S. Cl. .............................. 435/291; 435/311; 435/808; 422/52
[58] Field of Search ............ 435/291, 311, 808; 422/52

[56] References Cited
U.S. PATENT DOCUMENTS

| | | | |
|---|---|---|---|
| 3,359,973 | 12/1967 | Hoffman | 435/808 X |
| 3,690,837 | 7/1970 | Witz et al. | 435/808 X |
| 3,795,489 | 3/1974 | Warnick et al. | 422/52 |
| 3,923,462 | 12/1975 | Cavanagh | 422/52 X |
| 3,963,928 | 6/1976 | Zolmer | 422/52 X |
| 4,170,520 | 10/1979 | Weaver | 435/291 X |
| 4,396,579 | 8/1983 | Schroeder et al. | 435/291 X |
| 4,563,331 | 1/1986 | Losee et al. | 435/291 X |

Primary Examiner—Larry Jones
Attorney, Agent, or Firm—Ostrolenk, Faber, Gerb & Soffen

[57] ABSTRACT

The invention relates to an apparatus for registering the presence of bacteria, particularly under field conditions. The apparatus includes a plate (1), in which there is formed a luminescence chamber (2) which is defined at its opening (3) by a support lattice (5) carrying a filter (4), the lattice opening out into and being carrying sealingly against the plate (1) with the aid of a liquid-sealing and opaque collection vessel (6). The plate (1) includes a transparent portion (7) which is situated above or opposite the opening (3) of the chamber (2). There is a means (8) above the portion (7) for registering a light flux caused by luminescence, said means (8) being accommodated in an opaque housing (13) sealing against the plate (1), and there is an aperture plate (9) displaceably arranged above the portion (7) between the plate (1) and the means (8) to prevent unintentional exposure of the means. Bacteria are enriched from a liquid sample on the filter (4), a chemical treatment of the bacteria on the filter provides light in the chamber by luminescence, the luminescence in the chamber being dependent on the chemicals being retained in the chamber by filter (4). Registration of the light taking place electronically or on a light-sensitive, rapidly developing, photographic film, when the light image which the luminescence achieves is either registered electronically or is read off on the film in the form of a large or smaller light patch or in the form of a grey tone which can be compared with a grey tone scale to define a measure of the bacteria content.

5 Claims, 1 Drawing Figure

U.S. Patent  Jun. 9, 1987  4,672,039
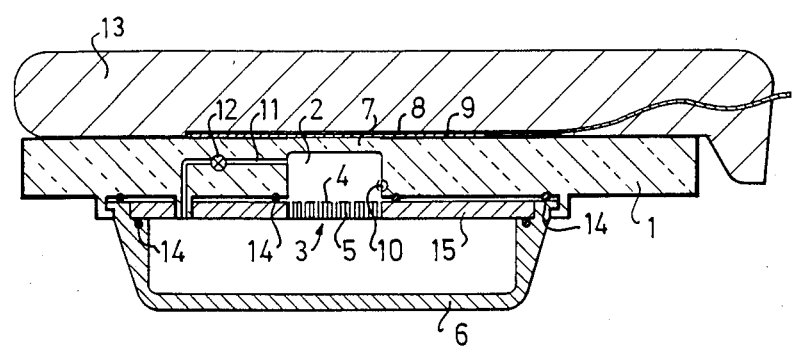

APPARATUS FOR REGISTERING THE PRESENCE OF BACTERIA, PARTICULARLY IN FIELD CONDITIONS

The present invention relates to an apparatus and a method for registering the presence of bacteria, particularly under field conditions, including a portable plate with a luminescence chamber preferably made in transparent material, in which a liquid sample including bacteria is caused to emit light by luminescence with the aid of certain chemical compositions, the light being read by a light-sensitive means arranged adjacent the luminescence chamber, and constituting a measure of the bacteria present in the liquid sample.

Such tests for the detection of bacteria usually take place by a sample that is suspected to contain bacteria being grown in a nutrient solution, so that the growth of cultures may be observed and counted therein. The method generally requires heat incubation and a time of between 18–48 hours, as well as pure laboratory conditions. By this method it has been possible, however, to make a species determination of the bacteria. Modern hygiene and technology within the areas which require control of bacteria amounts in our surroundings have so far been substantially dependent on these slow and exact methods for detecting bacteria in gases and liquids. In many connections there is a desire rapidly to determine the presence of bacteria, and particularly when large health risks can be present, e.g. in bacteriological warfare.

The Swedish National Defence Research Institute has demonstrated a rapid way of discovering the presence of bacteria by a method utilising the fluorescence which, inter alia, bacteria can emit on being treated with suitable chemicals. This method consists in first collecting and subsequently treating bacteria with the hemin in the bacteria thus being released. This hemin is thereafter permitted to react with oxygen and luminol, thus causing chemical luminescence. Existing luminescence registrating apparatus have high sensitivity and can often register individual photons, but the disadvantage with these apparatus is that they are very large and have a complicated construction; while also having a high price, and so far they have only been used in larger laboratories. For practical applications there is a desire for and a large need of being readily able to determine whether such as drinking water, bathing water, urine samples, wastewater, milk or other foodstuffs etc, contain alarming amounts of bacteria, or that they are uninfected and thus do not require any action.

The object of the present invention is to provide an apparatus for registering the presence of bacteria, particularly in field conditions, with which it is possible to obtain a reading by the registration of the amount of microorganisms, and to use the reading for a rough assessment of the type "serviceable" or "unserviceable" for a particular liquid sample. The apparatus in accordance with the invention is easily handled due to its simple construction, and may be used by untrained persons.

The invention accordingly intends to provide an apparatus of the kind mentioned in the introduction, which is easy to handle and at the same time cheap to manufacture. Essentially distinguishing for the invention is that the luminescence chamber, which is formed in the plate preferably made from transparent material, has its opening defined by a filter which is carried by a perforated support lattice and which opens out in an opaque collection vessel sealing liquid-tight against the plate, in that the plate includes a transparent portion, above or opposite the opening of the chamber, over which portion there is a means for registering a light flux generated by luminescence, said means being situated in an opaque housing sealing against the plate and covering the portion, and in that if photographic film is used, as the means, there is an aperture plate displaceably mounted above the portion, between the plate and the means, for preventing unintentional exposure of the means. The method, particularly for field determination of the presence of bacteria by the apparatus, is essentially distinguished in that a liquid sample is injected into the luminescence chamber and is urged against the filter arranged at the bottom of the chamber for enriching on the filter the bacteria existing in the sample, in that after opening the venting duct valve, the bacteria on the filter have sprayed over them in turn sodium hydroxide, luminol and perborate in previously determined amounts, whereon immediately after the addition of the perborate the light which occurs by luminescence in the chamber is allowed to be exposed to a light-sensitive means for photographic or electronic registration, the intensity of the light image achieved at the light-sensitive means being in proportion to the number of bacteria.

Thanks to the invention, an apparatus has been provided with the aid of which the presence of bacteria in a liquid sample can be very rapidly determined outside laboratories with sufficient accuracy for deciding whether closer analysis is required, the apparatus being very rapid, easily looked after, light, cheap, robust, cheap in operation and very simple, in comparison with all previously known apparatus.

The invention will be described below with reference to the accompanying drawing, which shows a preferred embodiment of an apparatus in accordance with the invention, as seen in cross-section.

As will be seen from the FIGURE the apparatus comprises, in accordance with the present invention, a thick plate 1 manufactured from a suitable transparent material, there being a luminescence chamber 2 in the plate. The chamber 2 in the illustrated embodiment is preferably milled in the plate and has a practically cylindrical shape. The opening 3 of the luminescence chamber 2 is defined by a filter 4 arranged on a perforated support lattice 5, the filter being of the polycarbonate type with accurately determined pore size. The filter 4, which rests on the support lattice 5 opens into and is carried sealingly against, the plate 1 with the aid of an opaque liquid-sealing collection vessel 6. The filter 4 and support lattice 5 as well as the collection vessel 6 are sealed by O rings 14 against the bottom of the plate 1. The plate 1 is entirely surrounded externally, by preferably light-insulating paint, although not in the chamber 2 nor in a portion 7 above or opposite the opening 3 of the chamber 2, this portion being transparent, and having a means 8 above it for registering light flux formed by luminescence. The means 8 may constitute a light-sensitive photographic film or a light-sensitive electronic cell in association with the portion 7 for registering the light image. The means 8 is accomodated in an opaque housing 13 sealing against the plate 1 and covering the portion 7. In the case where a photographic film is used, an aperture plate 9 is arranged between the housing 13 and the plate 1, this plate 9 being displaceable over the portion 7 between the plate 1 and the photographic film for preventing unintentional exposure. The luminescence chamber 2 has a communication duct 10 extending into it through the plate 1 for enabling the injection of a liquid sample and chemicals, the duct 10 opening out preferably tangentially in the chamber 2. From the roof of the chamber 2 or in the area closest to it, there is a venting duct 11 leading down into the collection vessel 6. This duct 11 may be closed by a valve 12. The collection vessel 6 is formed with a cover 15, in the central portion of which the support lattice 5 for the filter 4 is formed. The support lattice 5 is required when the chamber 2 is subjected to pressure which would otherwise rupture the filter 4.

The function of the apparatus in accordance with the present invention is as follows.

In sampling there are used one large, about 50 cc, and three smaller, about 2 cc, injection syringes without needles, of the type used for health care purposes, for filling the chamber 2 with the sample of bacteria-carrying liquid and for infecting the chemicals causing the luminescence. The syringes have the advantage that they are graduated for easily measuring and metering the sample and liquids. The diameter of the duct 10 has a dimension such that the conical tips of the syringes fit into it. The syringes are stored together with the apparatus or in a special apparatus case. A sample is taken of a given amount of liquid using the large syringe, e.g., 10 ml, and the rest of the syringe is filled with air. If the sample which is to be taken is heavily contaminated with larger particles it may need to be coarsely filtered by a disposable initial filter on the syringe. The sample is injected through the filter 4, which constitutes the bottom of the chamber 2. The filtrate runs down into the container 6 and the chamber 2 is flushed with air when the syringe is emptied. If bacteria were in the sample they have now been collected on the filter 4 on the separating filter surface at the bottom of the chamber 2. The bacteria collected on the filter 4 are then treated with sodium hydroxide (NaOH) which ruptures the cell membranes of the bacteria and thereby releases their content, including, inter alia, hemin. Luminol is then injected, and after about a minute, when the perborate is injected, the luminol starts the luminescence reaction with the hemin. Injection of the chemicals takes place with the valve 12 open, so that components in the chamber 2 will not be flushed through the filter 4. Dosing of the chemicals is done according to the directions for their use. Instead of sodium hydroxide, luminol and perborate, other chemicals with corresponding reactions may be used, of course. Immediately after the perborate has been injected, the aperture plate 9 is pulled out so that the ceiling of the chamber 2, or the transparent portion 7, is opened to expose the photographic film. In the case where the light-sensitive means 8 consist of an electronic cell the light caused by luminescence in the chamber is accumulated and registered electronically immediately after the start of the reaction, a value being obtained which corresponds to a measure of the bacteria present, and in the case where the light-sensitive means 8 consists of a photographic film the luminescence in the chamber 2 is allowed to continue for about 1½ minutes, after which the aperture plate 9 is closed and the film (of the polaroid type) is pulled out and developed for the prescribed time, generally 30-45 seconds, the picture then being removed and evaluated. If bacteria are present in the sample there is a round, white image on the film, the diameter of the image being in proportion to the number of bacteria detected. If a grey tone is used for detection, then the relation of this to a grey scale is decisive for a registered bacteria content. For electronic registration of the light caused by luminescence, the light is utilised via the plate 8, provided with cells, in a moving coil instrument or a digital indicator, the indication on which remains at the maximum value of light registered during the measuring period, this indication constituting a measure of the bacteria present.

I claim:

1. Apparatus of a portable kind for registering the presence of bacteria, particularly under field conditions, comprising;
    at least one luminescence chamber formed in a plate made of transparent material;
    said luminescence chamber having an opening which communicates with a filter which rests on a perforated support lattice held sealingly against said plate by a water-tight and opaque collection vessel, said luminescence chamber further having a communication duct for injecting a liquid sample and chemicals and a venting duct which passes from said luminescence chamber to said collection vessel, said venting duct being closable with the aid of a valve;
    the portion of said plate opposite said opening being transparent such that light flux created by luminescence within said luminscence chamber passes through said transparent portion and is incident onto means for registering said light, said means for registering being situated in an opaque housing sealed against said plate and covering said transparent portion of said plate.

2. Apparatus as claimed in claim 1, wherein the means for registering the light occurring due to luminescence comprises a light-sensitive photographic film.

3. Apparatus as claimed in claim 1 or 2, wherein an aperture plate is displaceably arranged between said portion of said plate and the light sensitive photographic film for preventing unintentional exposure of the film.

4. Apparatus as claimed in claim 1, wherein said means for registering the light occurring due to luminescence comprises an electronic light detector for registering the light generated by the reaction in the chamber.

5. Apparatus as claimed in claim 1, wherein said luminescence chamber is cylindrical in shape, and said communication duct for infecting a liquid sample and chemicals extends through said plate and passes tangentially into said luminescence chamber.

* * * * *